(12) United States Patent
Chaumot et al.

(10) Patent No.: US 11,609,221 B2
(45) Date of Patent: Mar. 21, 2023

(54) METHOD FOR DETECTING THE PRESENCE OF A CONTAMINANT IN A LIQUID

(71) Applicants: Institut National de Recherche Pour L'Agriculture, L'Alimentation et L'Environnement, Antony (FR); View Point, Civrieux (FR)

(72) Inventors: Arnaud Chaumot, Lyons (FR); Maxime Dauphin, Ceignes (FR); Alexandre Decamps, Saint-Gervais-sur-Mare (FR); Olivier Geffard, Perigny (FR); Florian Moulin, Lyons (FR); Didier Neuzeret, Sainte Euphemie (FR); Hervé Queau, Saint-Bonnet de Mure (FR)

(73) Assignees: INSTITUT NATIONAL DE RECHERCHE POUR L'AGRICULTURE, L'ALIMENTATION ET L'ENVIRONNEMENT, Antony (FR); VIEW POINT, Civrieux (FR)

(*) Notice: Subject to any disclaimer, the term of this patent is extended or adjusted under 35 U.S.C. 154(b) by 417 days.

(21) Appl. No.: 16/631,862

(22) PCT Filed: Jul. 18, 2018

(86) PCT No.: PCT/EP2018/069523
§ 371 (c)(1),
(2) Date: Jan. 17, 2020

(87) PCT Pub. No.: WO2019/016273
PCT Pub. Date: Jan. 24, 2019

(65) Prior Publication Data
US 2020/0150104 A1 May 14, 2020

(30) Foreign Application Priority Data

Jul. 18, 2017 (FR) .................................. 1756815

(51) Int. Cl.
*G01N 33/18* (2006.01)
(52) U.S. Cl.
CPC .................................. *G01N 33/186* (2013.01)
(58) Field of Classification Search
None
See application file for complete search history.

(56) References Cited

U.S. PATENT DOCUMENTS

| 4,164,199 A | 8/1979 | Pequegnat |
| 4,722,371 A | 2/1988 | Seagel et al. |
| 9,513,194 B2 * | 12/2016 | Baptista ............... G01N 33/186 |

FOREIGN PATENT DOCUMENTS

| CN | 101059493 | 10/2007 | |
| JP | 2010-529453 | * 8/2010 | ........... G01N 33/186 |
| WO | 2008150096 | 12/2008 | |

OTHER PUBLICATIONS

Blaxter et al., The Effect of Pollutants on Sensory Systems and Behaviour of Aquatic Animals, 26(1) Netherlands Journal of Aquatic Ecology 43-58 (1992).

(Continued)

*Primary Examiner* — Daniel S Larkin
(74) *Attorney, Agent, or Firm* — Panitch Schwarze Belisario & Nadel LLP; Erin M. Dunston

(57) ABSTRACT

The invention relates to an autonomous method for the online evaluation of the toxicity of aqueous solutions by analysis of the locomotor behavior of small-sized aquatic benthic macroinvertebrates (0.1 cm-5 cm) maintained in the lethargic state.

19 Claims, 6 Drawing Sheets

(56) References Cited

OTHER PUBLICATIONS

Figure 1:
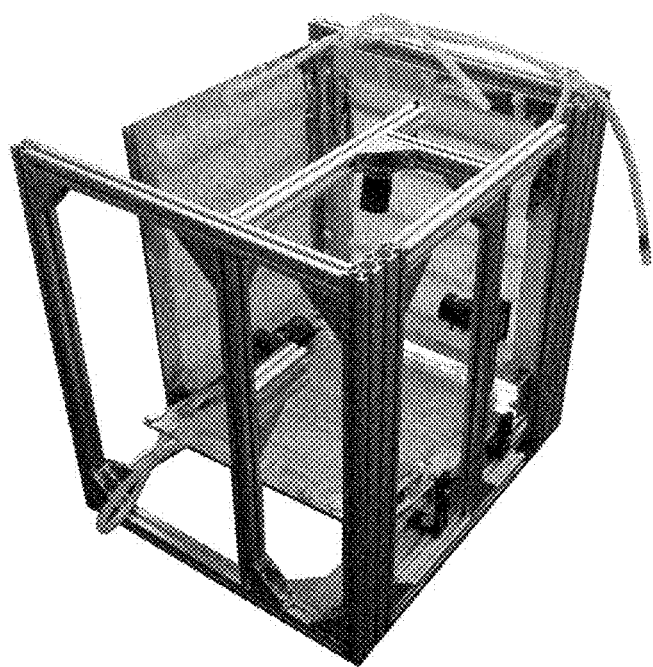

Cairns et al., Biological Monitoring Part 1 Early Warning Systems, 14 Water Research 1179-1196 (1980).

Chevalier et al., Can Daphnia behavioral endpoints be used as tool for ecotoxicological assessment of wastewater effluents?, https://hal-ineris.archives-ouvertes.fr/ineris-01862416 (2014).

Gerhardt, Monitoring Behavioural Responses to Metals in *Gammarus pulex* (L.) (*Crustacea*) with Impedance Conversion, 2(1) Environ Sci. & Pollut. Res. 15-23 (1995).

Gerhardt, Behavioural Early Warning Responses to Polluted Water, Performace of *Gammarus pulex* L. (*Crustacea*) and Hydropsyche angustipennis (Curtis) (Insecta) to a complex Industrial Effluent, 3(2) Environ. Sci. & Pollut. Res. 63-70 (1996).

Hellou et al., A non-lethal chemically based approach to investigate the quality of harbour sediments, 389 Science of the Total Environment 178-187 (2008).

Jeon et al., Development of a new biomonitoring method to detect the abnormal activity of Daphnia magna using automated Grid Counter device, 389 Science of the Total Environment 545-556 (2008).

Hellou, Behavioural ecotoxicology, an "early warning" signal to assess environmental quality, 18 Environ Sci Pollut Res 1-11 (2011).

Ren et al., The early warning of aquatic organophosphorus pesticide contamination by on-line monitoring behavioral changes of Daphnia magna, 134 Environ Monit Assess 373-383 (2007).

Robinson, E-waste: An assessment of global production and environmental impacts, 408 Science of the Total Environment 183-191 (2009).

Somom et al., Effects of Sublethal Cadmium Exposure on Antipredator Behavioural and Antitoxic Responses in the Invasive Amphipod Dikerogammarus villosus, 7(8) PLOS One 1-10 (Aug. 2012).

Henderson et al., Use of Fish in the Detection of Contaminants in Water Supplies, 55(6) American Water Works Association 715-720 (Jun. 1963).

Standard Methods for the Examination of Water and Wastewater, 1005—*Benthic Macroinvertebrates, Introduction*, 15th Edition (with English translation) (1980).

\* cited by examiner

METHOD FOR DETECTING THE PRESENCE OF A CONTAMINANT IN A LIQUID

The invention relates to an autonomous process for online evaluation of the toxicity of aqueous solutions by analysis of the locomotor behaviour of small (0.1 cm-5 cm) benthic aquatic macroinvertebrates maintained in a lethargic state.

CONTEXT AND TECHNOLOGICAL BACKGROUND

The quality of water resources is a major societal concern both from the point of view of environmental preservation and health. For this reason, the Member States of the European Union have set themselves crucial guidelines, namely treating wastewater (91/271/EEC), limiting the entry of priority substances into the environment (2013/39/EU), reducing the entry of contaminants at source and achieving "good status" of water bodies throughout the territory (WFD 2000/60/EC).

Although the majority of urban and industrial discharges go through a treatment phase, these are now designed to eliminate mainly organic matter and limit the eutrophication of aquatic environments related to the input of nitrogen and phosphorus, depending on the sensitivity of the receiving hydrosystem. However, discharges remain an important vector for the entry of contaminants (micropollutants) into the environment (Cairns and Van Der Schalie, 1980), constituting a major issue today for wastewater treatment managers and a key element in the protection of the environment and the preservation of water resources.

The principle of "monitoring wastewater collection systems and treatment plants in order to maintain and verify their efficiency" by local authorities has been established since 1991 by the European Directive on Urban Wastewater Treatment (UWWT). Recent changes in French legislation, notably the ministerial order of 21 Jul. 2015, require a self-assessment approach at the level of the sanitation system. Today, these self-assessment systems are based on punctual sampling, averaged over 24 hours, which does not allow to know the dynamic operation of the station.

In anticipation of stricter legislation and with the aim of limiting the input of contaminants into the environment, there is a real demand for a tool to analyse the quality of discharges online from public and private water managers. Beyond the regulatory aspect, the development of self-monitoring tools would be a real opportunity to refine the managers' knowledge on their discharges, especially their evolution over time, and to characterize in real time their quality in order to optimize the management of sanitation systems.

In order to obtain a comprehensive, robust and environmentally meaningful assessment, ecotoxicological values are chosen. Chemical analyses, with current techniques and for the characterization of discharges, seem difficult because of the strong temporal heterogeneities and the large number of molecules that compose them (Cairns and Van Der Van, 1980; Sornom, 2012). Moreover, simply knowing the concentrations of a few products is not sufficient to produce useful management information (Cairns and Van Der Schalie, 1980), so the use of biological tools, which integrate all environmental factors and the bioavailable portion of contaminants present in the discharge, is more promising. Furthermore, online assessment of the quality of discharges without the need for spot sampling as is currently the case for Afnor standardized toxicity tests would make it possible to avoid many of the current limitations of bioassessment (spot assessment, denaturation of samples during transport and storage, long response time).

The use of biological tools, including locomotor behaviour analysis to assess the toxic quality of discharges is a robust and adequate solution since this biomarker is known to be ubiquitous, generalist and have a very short response time (Blaxter and Hallers-Tjabbes, 1992; Hellou, 2011). This biomarker is based in particular on the organism's chemoreceptor responses (Gerhardt, 1996). Online monitoring of locomotor behaviour makes it possible to detect lower concentrations of contaminants than conventional lethality studies (10-1000 times more sensitive) (Hellou et al., 2008; Robinson 2009) and to know, with a small time step, the toxicity of discharges before they are released into the natural environment.

The idea of using aquatic macroorganisms to assess the ongoing toxicity of aquatic environments is not new. Devices began to develop based on monitoring fish (Henderson and Pickering, 1963) and then refined to track invertebrates such as *Gammarus, Hydropsyche* (Gerhardt, 1996), *Daphnia* (Ren et al. 2007; Jeon et al., 2008, Chevalier, 2014). All of this work supports the relevance of the use of the biomarker of locomotor activity in the early and sensitive assessment of contaminants in water. Now that the proof of relevance is no longer to be made, it is necessary to adapt this concept of tools to the analysis of waste water and to make them autonomous. To do this, important obstacles must be overcome, namely the design of a device that allows long-term monitoring of several macroorganisms simultaneously, over a period of several weeks, and that is suitable for receiving discharge water (FIG. 1). It is also necessary to develop a toxic signal suitable for online and on-site assessment of urban and industrial discharges. The latter must detect low concentrations of contaminants while excluding confounding factors intrinsic to the conditions of exposure, namely the presence of vibrations at industrial or urban sites (pump, human activity, vehicle passage, etc.) and natural variations in the physicochemical composition of major ions in the discharge water, which may affect the locomotor behaviour of the bioassays.

One of the analytical procedures consists of monitoring these living macroorganisms throughout the exposure period to study their behaviour, and to continuously infer the toxicity of the test medium throughout the exposure period. For this purpose, an organism is arranged in a container that is transparent on at least one observation side, and images of the container are acquired through the observation side by an imager arranged opposite the observation side.

However, in the case of living organisms, there is some uncertainty as to the response of the living organism to the exposure of the potentially toxic discharge under consideration, or even their inevitable loss. It is therefore necessary to study several living beings simultaneously and to statistically process the results in order to erase these hazards. However, it is generally not appropriate to place several living organisms in the same container as macroorganisms may interfere with each other, which may complicate the interpretation of monitoring results.

SUMMARY OF THE INVENTION

The principle of the process of the invention is based on the lethargic state of the macroorganisms before their exposure under stable and controlled observation conditions. This lethargy corresponds here to minimal locomotor behaviour of the species observed and a lack of nutritional activity (extreme reduction in locomotion, lack of foraging and feeding behaviour). The presence of contaminants in the exposure environment then results in an exit from this state of lethargy due to the chemoreception capacities of the organisms used and the avoidance behaviour in the face of the chemical stress that follows. The process of the invention does not a priori require a control liquid. To ensure the robustness of the detection of this exit response from the lethargic state, it is advantageous to study a batch of individuals homogeneous with regard to their biological characteristics: individuals calibrated in sex, size, reproductive status, coming from a single population, preferably housed in the laboratory before transplantation in the observation chambers. It is also necessary that the living beings maintain this homogeneity during the observation period (absence of moulting, oviposition, growth). This lethargic state cannot be reached by organisms such as *Daphnia*, which by definition are always in motion and a lack of locomotion is synonymous with death. The organisms that can reach this state are benthic aquatic macroinvertebrates.

The process of the invention is particularly advantageous because it allows online toxicity evaluation in an autonomous manner between 2 and 30 days of follow-up with a frequency of evaluation in small time steps (from 2 to 120 minutes).

BRIEF DESCRIPTION OF THE DRAWING FIGURES

FIG. 1: Photograph of the toximeter developed by Irstea-ViewPoint

Figure 2:
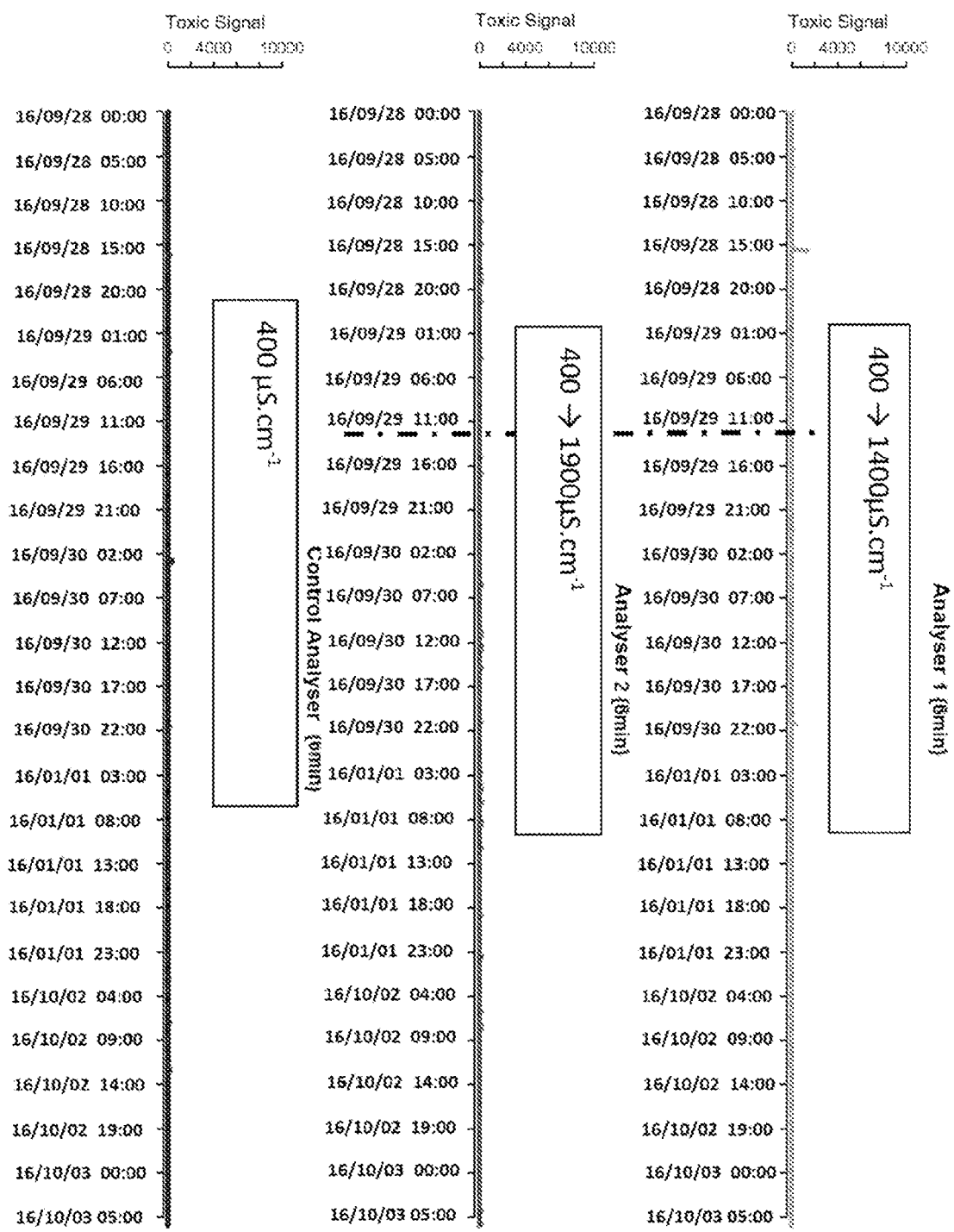
Figure 3:
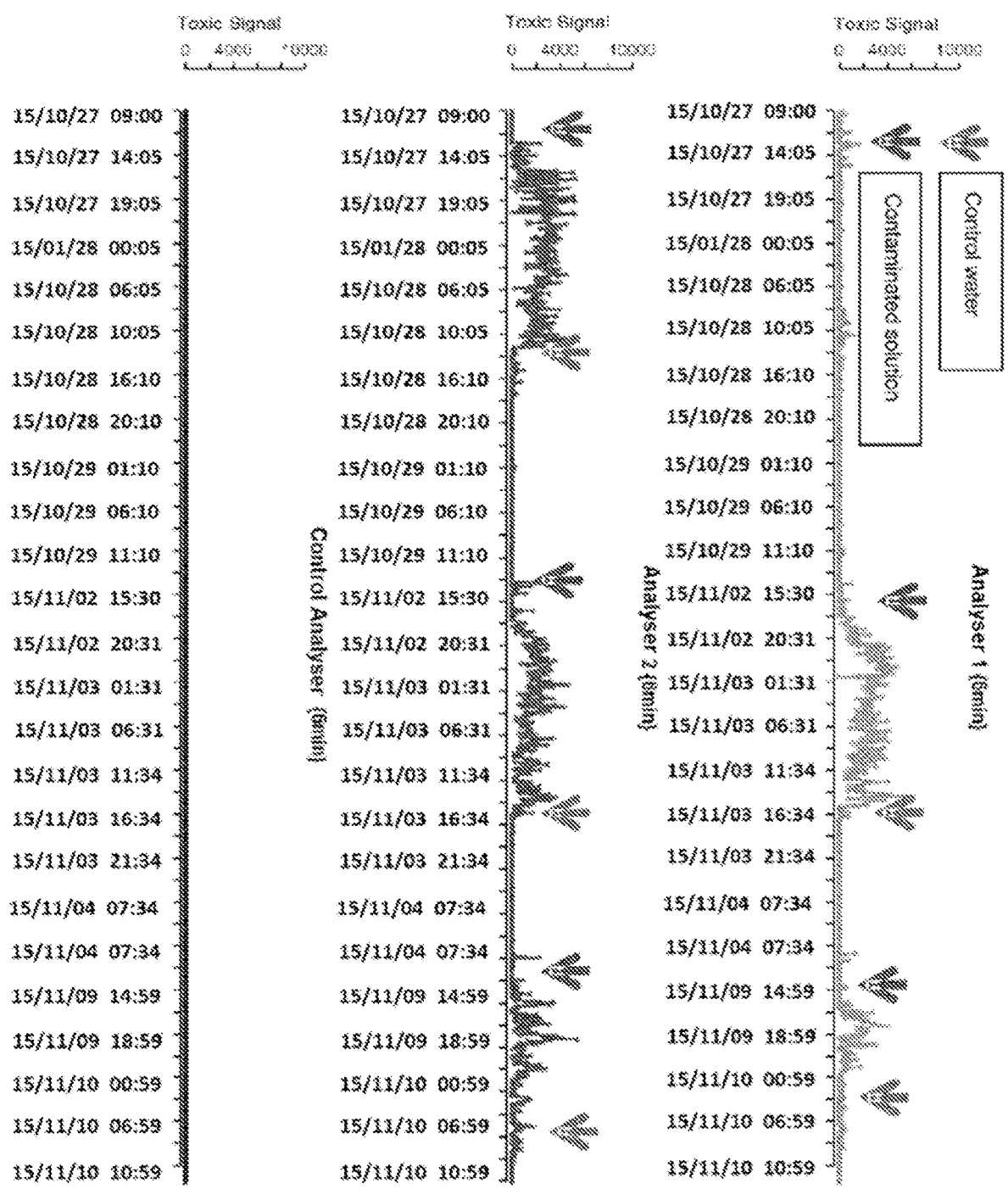

FIG. 2: Recording graph of the change in locomotor index during abrupt changes in conductivity FIG. 3: Change in locomotor index over 3 weeks during the periodic addition of methomyl-contaminated solution (100 μg/L)

Figure 4:
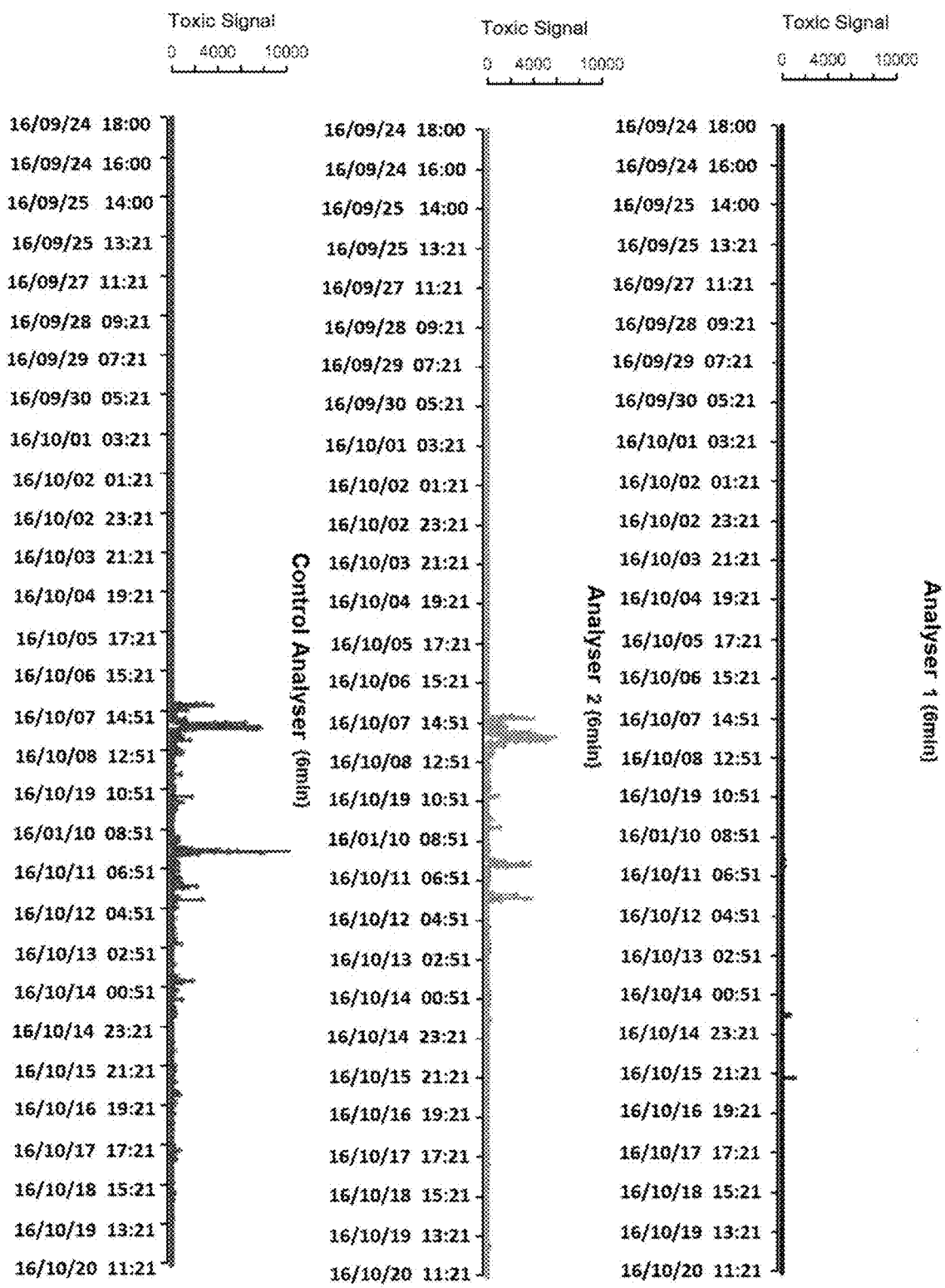

FIG. 4: Monitoring the toxic quality of treated water at the outlet of a wastewater treatment plant over a 28-day period.

Figure 5:
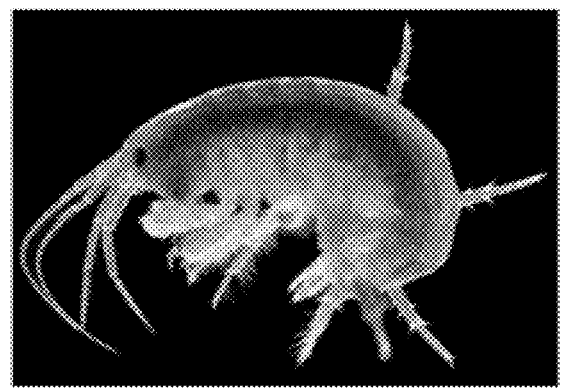

FIG. 5: Photograph of *Gammarus fossarum* (amphipod of the family Gammaridae 8-30 mm)

Figure 6:

FIG. 6: Photograph of *Erpobdella testacea* (annelid subclass Hirudinea (leech) 15-40 mm)

Figure 7:
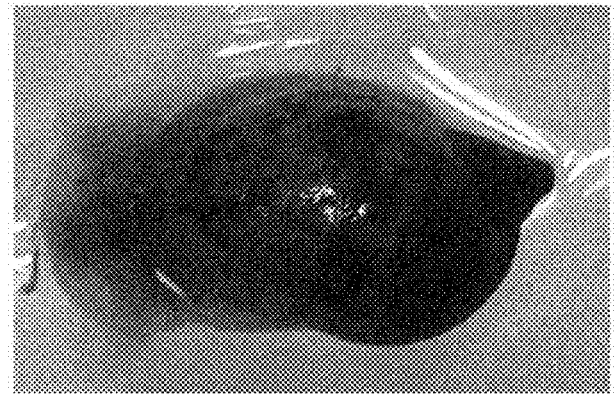

FIG. 7: Photograph of *Radix auricularia* (pulmonate gastropod 6-30 mm)

Figure 8:
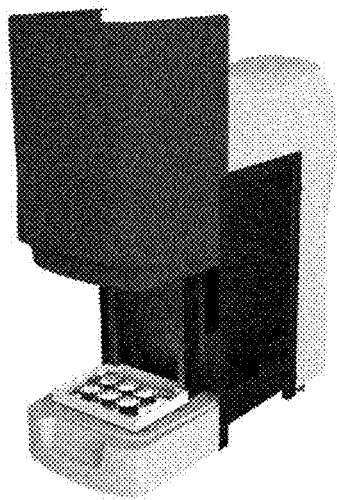

FIG. 8: Photograph of a ZebraBox

DEFINITIONS

For the purposes of the present invention, "movement" means a change of position in space. This change can be characterized in many ways such as measuring a distance travelled, speed, rotation, changes in the orientation of a whole body or one of its parts (head, leg, etc.).

For the purposes of the present invention, "behaviour" means a measure of movement per unit of time.

For the purposes of the present invention, lethargy means the state of a batch of individuals characterized by:
  an average behaviour (i) constant over a period of at least six hours, preferably 12 hours, and (ii) decreased by at least 60%, preferably 80% and advantageously by 90% compared to the behaviour measured during the first hour of observation of the batch of individuals, and
  an absence of nutritional activity.

For the purposes of the present invention, emergence from lethargy means the increase in the average behaviour of a batch of individuals by at least a factor of two over a period of at least 10 minutes.

For the purposes of the present invention, "housing" means maintaining benthic aquatic macroinvertebrates under controlled conditions (pH, feeding, conductivity, luminosity) in order to homogenize the batch of individuals used during the experiment (energy reserves, physiological state) and eliminate individuals weakened during collection, and to condition them for future exposure conditions.

For the purposes of the present invention, "locomotor index" corresponds to an average distance calculated according to the study context (field or laboratory) over the 10% to 80% of the lowest values of individual distances travelled. The locomotor index is the average of these shortest distances. This locomotor index is calculated on an integration time step that can be chosen between 2 and 120 minutes. The values of distances travelled are squared before the index is calculated, so the locomotive index is expressed in $mm^2$/unit of time.

For the purposes of the present invention, "contaminant" means all chemical substances (plant protection products, heavy metals, PAHs, organic pollutants, drug residues, etc.) capable of causing avoidance behaviour in exposed benthic aquatic macroinvertebrates.

DETAILED DESCRIPTION

The invention relates to a process for detecting the presence of a contaminant in a liquid, preferably water, comprising the following steps:
  a) conditioning a batch of small benthic aquatic macroinvertebrates to enter a lethargic state;
  b) immersing said benthic aquatic macroinvertebrates in the liquid, each organism being isolated individually;
  c) continuously recording the behaviour of each aquatic organism during exposure;
  d) analysing by means of a processing device the behavioural data to determine the behaviour of benthic aquatic macroinvertebrates;
  e) determining on the basis of the behaviour of benthic aquatic macroinvertebrates the presence of toxic contaminants;
  characterized in that the analysis of the data comprises the determination, for each of the species of said benthic aquatic macroinvertebrates, of an average behaviour representative of the movements of the benthic aquatic macroinvertebrates of this species over a given period of time, the benthic aquatic macroinvertebrates being placed during the observation period under conditions in which the absence of toxicity results in the maintenance of the entire batch of benthic aquatic macroinvertebrates in a lethargic state, said conditions being favourable to the maintenance of life of said benthic aquatic macroinvertebrates and comprising an absence of food supply during the observation period,
  and in that the determination of the presence of toxicity comprises comparing said average behaviour to the average behaviour of the lethargic state, the presence of toxicity being established when the average behaviour increases by at least a factor of two over a period of at least 10 minutes.

The benthic aquatic macroinvertebrates may be placed in suitable conditions of absence of stimuli to reach a lethargic state. The species used in the process of the invention must be capable of being kept alive for a period of at least one week in a partitioned environment, under constant light conditions and temperature, without food supply, without change of development stage (moulting, metamorphosis, etc.) or reproductive events (laying, asexual reproduction).

The process of the invention is particularly advantageous because it is autonomous over a prolonged period of at least two days, preferably at least two weeks and particularly preferred 30 days.

Each aquatic benthic macroinvertebrate is isolated individually in an observation chamber to ensure that data from one individual are not disturbed by the presence of one or more other individuals and to ensure a robust assessment by having a large number of replicates.

Advantageously, at least 12 benthic aquatic macroinvertebrates, preferably at least 16 benthic aquatic macroinvertebrates, per species are included in the process of the invention and observed (FIG. 1).

Preferably, in step c) the behaviour of each benthic aquatic macroinvertebrate is recorded by simultaneous image acquisition using an imager or by impedance measurement ("Monitoring Behavioural Responses to Metals in *Gammarus pulex* (L.) (Crustacea) with Impedance Conversion, Almut Gerhardt, Environ. Sci. And Pollut. Res. 2(1), 1995).

The images are analysed and the locomotor index is calculated continuously and transmitted online (on a website) in real time.

Preferably, the process according to the invention is preceded by a step prior to step a) of selecting benthic aquatic macroinvertebrates so that each species represents a population of living beings that is as homogeneous as possible: calibrated in terms of sex, size, reproductive status, non-parasitized. Advantageously, the individuals of each species come from a single population.

It is also necessary that this population of living beings maintains its homogeneity: no moulting, no laying, no feeding.

The energy reserves of the selected benthic aquatic macroinvertebrates allow them to be kept alive throughout the entire period of implementation of the process according to the invention without food supply, preferably for at least one week, particularly preferred for one month. Thus, the image acquisition is not disturbed by a food supply in the liquid. *Daphnia* are not adapted to the process of the invention since they do not support a prolonged diet.

Preferably, the benthic aquatic macroinvertebrates are preselected to represent a population that is homogeneous in size, sex and non-parasitized.

Preference will be given to individuals that will not have young during the process, for example, individuals of non-female sex or sexually immature, in order to avoid the production of young in the liquid that will disturb the acquisition of the images.

Preference will be given to individuals that do not mutate during the process.

Preferably, benthic aquatic macroinvertebrates should be staged prior to step b) in order to acclimatize them to the measurement conditions.

Said benthic aquatic macroinvertebrates may belong to the same species or be selected from several species, preferably of different phylogenetic orders, preferably up to three species.

Said benthic aquatic macroinvertebrates are small in size, preferably less than 5 cm, preferably less than 2 cm, particularly preferred less than 1 cm.

Advantageously, gastropods, leeches and/or crustaceans are preferred.

Preferably, the gastropod species is of the genus Radix, preferably *Radix auricularia*.

Preferably, the leech species is of the order Arhynchobdellida, preferably of the family Erpobdellidae, for example *Erpobdella testacea*.

Preferably, the crustacean species is an amphipod, preferably of the family Gammaridae, for example *Gammarus fossarum*.

Advantageously, said benthic aquatic macroinvertebrates have a survival rate of more than 80% at 30 days of diet under the physicochemical conditions of the process of the invention without contaminant.

Preferably, images are acquired in step c) every 66 mS (15 hertz) and integrated over 20 seconds.

EXAMPLES

In the examples, only benthic aquatic macroinvertebrates calibrated in terms of size, sex, non-parasitized, from a single population and housing for two weeks in the laboratory are shown. The benthic aquatic macroinvertebrates are placed in a cage under camera monitoring where 16 individuals are placed alone in a volume of 50 mL of water.

The cage is made of neutral materials (polypropylene) and without the use of toxic products (no glue). These cages (FIG. 1) are connected to a pre-bubbled, thermo-regulated and filtered liquid supply and then circulate in the chamber that receives the effluent at a flow rate of 6 L/h.

During the exposure period (30 days), the benthic aquatic macroinvertebrates are exposed under conditions favourable to their maintenance (13±2° C., oxygen-saturated and predator-free) and put on a diet to homogenize their behaviour (the energy reserves of the selected benthic aquatic macroinvertebrates allow them to remain alive for one month under these conditions).

One of the possible applications of online assessment of the toxicity of a liquid by analysing the escape behaviour of benthic aquatic macroinvertebrates is the analysis of urban or industrial waste water at the end of treatment. The tool is designed to be transportable and to perform the measurements on site in order to have a live and continuous evaluation. An initial experiment was carried out in a wastewater treatment plant in order to integrate into the monitoring of the toxicity of treated water all the factors that can influence the behaviour of benthic aquatic macroinvertebrates by activating them and bias the toxicity assessment (vibrations from pumps, human activities, vehicle passages, etc.). In addition, treated water has natural physicochemical variations over time (depending on discharges into the catchment area, rainy episodes, treatment plant operation, etc.). In order to measure the influence of these two factors, namely on-site disturbances and physicochemical variations, three toximeters were placed in a treatment plant connected with uncontaminated water for 9 days. The first two days allow the biological probes to reach a lethargic state characterized by inactivity, which are not presented in this result.

After these two days, the toxicity monitoring starts. On the fourth day, salt-enriched solutions were added abruptly to toximeters 1 and 2 in order to increase the conductivity to 400 $\mu S \cdot cm^{-1}$ at 1400 and 1900 $\mu S \cdot cm^{-1}$, respectively. These changes in conductivity were measured continuously by a conductivity meter. The follow-ups of the three toximeters are shown in FIG. 2. The locomotor index of each of the toximeters shows no change during strong variations in conductivity or during the whole experiment due to vibration disturbances caused by the intrinsic activity of the station. Experience has shown that the toxicity analysis method developed excludes two important confounding factors, namely variations in conductivity over time and the presence of disturbances due to the activity of the treatment plant. This tool and the calculation method are thus suitable for the online assessment of the toxicity of treated water.

An experiment was conducted to verify the detection of toxicity by the toximeter and its method of calculating the locomotor index. Three toximeters are connected to uncontaminated water, then toximeter 1 receives one contamination episode of 20-24 h at weeks 1, 2 and 3, toximeter 2 receives one contamination episode of 20-24 h at weeks 2 and 3 and toximeter 3 serves as a control to ensure that potential activation of the biological probes does not result from a disturbance (strong vibration). The contamination episode corresponds to the addition of an insecticide, methomyl, at a concentration of 100 µg·L$^{-1}$. This concentration is chosen high to be sure to observe effects on the locomotor behaviour of selected benthic aquatic macroinvertebrates (LC50 in *Daphnia* at 28 µg·L$^{-1}$ after 48 h exposure). The three follow-ups are presented in FIG. 3. It is observed that the monitoring method makes it possible to detect a toxicity of the product within 3 h, even after several episodes of contamination. It is important to note that these concentrations, in a wastewater treatment plant outlet environment, may be typical.

After validating that the locomotor index developed detects the toxicity of contaminants at environmental concentrations and that it is insensitive to variations in major ion content, the toxicity of water leaving the treatment plant was monitored. Two toximeters were connected in line on discharges from a treatment plant and one was connected to uncontaminated water to ensure a control condition on site. The monitoring is shown in FIG. 4. This monitoring shows that the device developed allows the locomotor activity of benthic aquatic macroinvertebrates to be monitored autonomously for one month in the toximeter when it is connected to water at the treatment outlet (turbid water, high TSS content). The control showed a constant and very low locomotor index along the follow-up corresponding to the maintenance of the lethargic state of the batch of individuals exposed on site. In contrast, the two toximeters, connected to the same discharge water in parallel to this control, simultaneously detect two episodes of exit from the lethargic state tracing a degradation of the toxic quality of the effluents; a first one on Oct. 7, 2016 from 11:30 am to 4 pm and a second one on Oct. 10, 2016 from 10 am to 12:30 pm. The tool and the method developed thus allow online monitoring of the toxic quality of an aqueous solution in an autonomous manner by analysing the escape behaviour of benthic aquatic macroinvertebrates.

The steps of this assessment are successively the selection of species, collection, housing for two weeks, sorting (calibration), caging, placing the toximeter in the effluent and continuous individual analysis of the locomotor behaviour of benthic aquatic macroinvertebrates.

Example 1: Species Selection, Collection, Housing and Sorting of Benthic Aquatic Macro in Vertebrates I. Materials
SPECIES SELECTION: fish net, sieve column, polyethylene buckets, facility for housing at 13° C. in a 16 L aquarium.
COLLECTION: fish net, vacuum sieve column with 1.6 mm, 2 mm, 2.5 mm mesh and a screen, polyethylene buckets.
HOUSING: facility for housing at 13° C. in 16 L aquariums.
SORTING: light table; transparent Pyrex dishes; mesh; landing net; polypropylene buckets (food buckets type), polystyrene plate.

II. Method

II.1. Species Selection

Species selection is a critical step since it directly affects the relevance of the toxicity assessment. The selection criteria verified on the stock of species tested in the laboratory are described below with their justification:

correspondence between the distribution area of the species and the study site so as not to bring biological pollution into the aquatic environment in the event of an accident.

present in high quantities in the environment throughout the year so that it is not limited at any given time by the organism pool.

which can survive more than 30 days on a diet because the toximeter is intended to be independent over a month and the presence of a food supply would alter the quality of the video tracking.

different phylogenetic order, representative of riparian biodiversity, and sensitive to the presence of contaminants. By increasing species diversity, the spectrum of susceptibility to contaminants is greater with different sensitivities. Assessment using this toximeter is relevant since it is environmentally representative.

behaviour that can be measured continuously and over time in order to obtain an online diagnosis and to rapidly notify managers in the event of problems.

one species placed horizontally and two others vertically to optimize the space in the toximeter (30 cm cube).

easy to handle, transportable and stackable so that installation remains easy.

The benthic aquatic macroinvertebrates selected for toxic assessment of discharges in Europe are *Gammarus fossarum* (FIG. 5), which is placed in the horizontal cage, *Erpobdella testacea* (FIG. 6) and *Radix auricularia* (FIG. 7) are placed in the vertical cages.

II.2. Collection of Benthic Aquatic Macroinvertebrates

The benthic aquatic macroinvertebrates come from a source population with high densities throughout the year. In the example developed, the organisms come from the former Bugey watercress field in the town of Saint-Maurice-de-Remens, in the department of Ain, which was defined as a collection station.

Collection is carried out using a steady-state disturbance in the different habitats of each species.

The sample collected at the bottom of the turbulence is then placed on the 1.60 mm, 2.00 mm, 2.50 mm mesh vacuum sieve column and the screen. Rinsing on the sieve column is then carried out using a bucket and then directly in the river. Benthic aquatic macroinvertebrates are contained in the various sieves.

This operation is repeated several times depending on the quantity of benthic aquatic macroinvertebrates desired.

II.3. Housing of Benthic Aquatic Macroinvertebrates Prior to Implantation in the Toximeter Before housing, each species is separated from other benthic aquatic macroinvertebrates, plant debris and minerals. They are then placed in 16 L aquariums containing site water that is drip-renewed (volume renewed four times a day) with fresh borehole water with a conductivity of 450 µS·cm$^{-1}$, oxygenated through continuous bubbling. The aquarium is placed in a water bath thermo-regulated at 13±1° C., exposed to a photoperiod of 14 hours day/10 hours night. Feeding is carried out ad libitum and the recommended housing time is two weeks. The objective of housing is to eliminate benthic aquatic macroinvertebrates that are weakened during collection, to ensure a certain "physiological homogeneity" of the benthic aquatic macroinvertebrates used regardless of the season (energy reserves, rates of behavioural activity such as locomotion, feeding), and to acclimatize them to future exposure conditions. The characteristics of the housing water are as follows: temperature=13±1° C.; conductivity=450±50 µS·cm$^{-1}$; pH=7.6±0.2; photoperiod=14 h day/10 h night. The benthic aquatic macroinvertebrates are placed in the dark for the last two days before installation in the toximeter.

II.4. Sorting of Benthic Aquatic Macroinvertebrates (Calibration)

Preparation of the benthic aquatic macroinvertebrates is done in the laboratory a few days before exposure. The benthic aquatic macroinvertebrates selected are male (for *Gammarus*, Radix and leeches are hermaphroditic), non-parasitized and of uniform size for each species. Sorting is carried out on a light table with water from the housing medium. Sexing is done with the naked eye. Benthic aquatic macroinvertebrates are separated and placed with suitable food in a polypropylene cage, a material with no toxic effect.

Using a mesh, the benthic aquatic macroinvertebrates are sorted according to the size, sex and non-parasitized criteria of each species and then transferred to the second dish. Only those *Gammarus* that have just moulted can integrate the toximeter to avoid activation due to moulting.

Step 2: Setting Up the Experiment

A facility should be installed at the study site to monitor the locomotor behaviour of benthic aquatic macroinvertebrates. The benthic aquatic macroinvertebrates are placed individually in cells to monitor the locomotor behaviour of benthic aquatic macroinvertebrates. The Toximeter or the ZebraBox® (FIG. 8) (Viewpoint, http://www.viewpoint.fr/en/p/equipment/zebrabox) is suitable for this kind of monitoring. The solution to be tested is prefiltered (<500 µm), bubbled and thermoregulated.

The toximeters or the ZebraBox® units are connected to the solution to be tested and the online evaluation of the toxic quality starts 48 hours after installation of the biological probes and the power supply for the measuring tools (toximeter or ZebraBox®).

Each ZebraBox® is equipped with one camera and the Toximeter is equipped with 3 cameras (one for each side).

The cameras continuously film the individual movements of the benthic aquatic macroinvertebrates.

A computer processes the images and calculates the locomotor index in real time.

A toxic quality assessment can be provided between every 2 and 120 minutes.

The online toxicity assessment is done autonomously and can last between 2 and 30 days. The computer connected to the internet communicates the results live on a website.

If toxicity is detected, the person responsible for the operation of the tool can be notified (SMS, e-mail, etc.).

In the case of a non-connection, the data is archived in an SD card.

The invention claimed is:

1. A process for detecting the presence of a contaminant in a liquid comprising the following steps:
   a) conditioning a batch of benthic aquatic macroinvertebrates with a size of 0.1 cm to 5 cm to enter a lethargic state;
   b) immersing said benthic aquatic macroinvertebrates in the liquid, each organism being isolated individually;
   c) continuously recording the behaviour of each aquatic organism during exposure;
   d) analyzing by means of a processing device the behavioural data to determine the behaviour of benthic aquatic macroinvertebrates
   e) determining on the basis of the behaviour of benthic aquatic macroinvertebrates the presence of toxic contaminants;

characterized in that the analysis of the data comprises the determination, for each of the species of said benthic aquatic macroinvertebrates, of an average behaviour representative of the movements of the benthic aquatic macroinvertebrates of this species over a given period of time, the benthic aquatic macroinvertebrates being placed during the observation period under conditions in which the absence of toxicity results in the maintenance of the entire batch of benthic aquatic macroinvertebrates in a lethargic state, said conditions being favourable to the maintenance of life of said benthic aquatic macroinvertebrates and comprising an absence of food supply during the observation period, and in that the determination of the presence of toxicity comprises comparing said average behaviour to the average behaviour of the lethargic state, the presence of toxicity being established when the average behaviour increases by at least a factor of two over a period of at least 10 minutes.

2. The process as claimed in claim 1, characterized in that in step c) the behaviour of each aquatic organism is recorded by simultaneous image acquisition using an imager.

3. The process as claimed in claim 1, said benthic aquatic macroinvertebrates being selected from one or more species of different phylogenetic orders.

4. The process as claimed in claim 3, said benthic aquatic macroinvertebrates being selected from one to three species of different phylogenetic orders.

5. The process as claimed in claim 1, said benthic aquatic macroinvertebrates being selected from gastropods, leeches, and/or crustaceans.

6. The process as claimed in claim 5, said gastropods being of the genus Radix.

7. The process as claimed in claim 6, said gastropods being of the genus *Radix auricularia*.

8. The process as claimed in claim 5, said leeches being of the order Arhynchobdellida.

9. The process as claim in claim 8, said leeches being of the family Erpobdellidae.

10. The process as claim in claim 8, said leeches being *Erpobdella testacea*.

11. The process as claimed in claim 5, said crustaceans being amphipods.

12. The process as claimed in claim 11, said crustaceans being of the family Gammaridae.

13. The process as claimed in claim 11, said crustaceans being *Gammarus fossarum*.

14. The process as claimed in claim 1, comprising a step prior to step a) of selecting benthic aquatic macroinvertebrates so that each species represents a population which is homogeneous in size, sex, and non-parasitized.

15. The process as claimed in claim 1, each species of benthic aquatic macroinvertebrates coming from a single population.

16. The process as claimed in claim 1, having a step of housing prior to step b) of said benthic aquatic macroinvertebrates in order to acclimatize them to the measurement conditions.

17. The process as claimed in claim 1, said benthic aquatic macroinvertebrates not being female benthic aquatic macroinvertebrates.

18. The process as claimed in claim 1, said benthic aquatic macroinvertebrates having a survival rate of more than 80% at 30 days of diet.

19. The process as claimed in claim 1, wherein said liquid is water.

* * * * *